US 8,885,907 B2

(12) United States Patent
Lenox

(10) Patent No.: US 8,885,907 B2
(45) Date of Patent: Nov. 11, 2014

(54) EMISSION COMPUTED TOMOGRAPHY FOR GUIDANCE OF SAMPLING AND THERAPEUTIC DELIVERY

(71) Applicant: The Texas A & M University System, College Station, TX (US)

(72) Inventor: Mark W. Lenox, College Station, TX (US)

(73) Assignee: The Texas A&M University System, College Station, TX (US)

( * ) Notice: Subject to any disclaimer, the term of this patent is extended or adjusted under 35 U.S.C. 154(b) by 150 days.

(21) Appl. No.: 13/671,305

(22) Filed: Nov. 7, 2012

(65) Prior Publication Data

US 2013/0308845 A1    Nov. 21, 2013

Related U.S. Application Data

(60) Provisional application No. 61/556,590, filed on Nov. 7, 2011.

(51) Int. Cl.
| | |
|---|---|
| *G06K 9/00* | (2006.01) |
| *A61N 5/10* | (2006.01) |
| *G06T 11/00* | (2006.01) |
| *G06T 7/00* | (2006.01) |

(52) U.S. Cl.
CPC ............ *A61N 5/1039* (2013.01); *G06T 11/003* (2013.01); *G06T 7/0012* (2013.01); *A61N 5/1049* (2013.01); *A61N 5/1067* (2013.01); *A61N 2005/1052* (2013.01)
USPC .................................. 382/131; 378/4; 378/21

(58) Field of Classification Search
None
See application file for complete search history.

(56) References Cited

U.S. PATENT DOCUMENTS

| | | | | |
|---|---|---|---|---|
| 6,765,983 | B2 * | 7/2004 | Yan et al. | 378/8 |
| 2002/0034276 | A1 * | 3/2002 | Hu et al. | 378/8 |
| 2004/0131140 | A1 * | 7/2004 | Bruder et al. | 378/4 |
| 2005/0058240 | A1 * | 3/2005 | Claus | 378/22 |
| 2005/0238133 | A1 * | 10/2005 | Koppe et al. | 378/4 |
| 2006/0210131 | A1 * | 9/2006 | Wheeler et al. | 382/128 |
| 2007/0116344 | A1 * | 5/2007 | Hsieh et al. | 382/131 |
| 2007/0165769 | A1 * | 7/2007 | Goto et al. | 378/4 |
| 2007/0183642 | A1 * | 8/2007 | Ye et al. | 382/131 |
| 2009/0214090 | A1 * | 8/2009 | Hayes | 382/128 |
| 2009/0290774 | A1 * | 11/2009 | Shechter et al. | 382/131 |
| 2010/0121183 | A1 * | 5/2010 | Taguchi et al. | 600/427 |
| 2010/0295846 | A1 * | 11/2010 | Schaefer et al. | 345/419 |
| 2011/0007958 | A1 * | 1/2011 | Salomon et al. | 382/131 |
| 2011/0082368 | A1 * | 4/2011 | Botterweck | 600/425 |
| 2011/0268339 | A1 * | 11/2011 | Volokh et al. | 382/132 |
| 2012/0114217 | A1 * | 5/2012 | Mistretta et al. | 382/133 |
| 2014/0148694 | A1 * | 5/2014 | Mistretta et al. | 600/432 |

* cited by examiner

*Primary Examiner* — Shervin Nakhjavan
(74) *Attorney, Agent, or Firm* — Saliwanchik, Lloyd & Eisenschenk

(57) ABSTRACT

Treatment for a variety of diseases often requires guidance for the delivery of either a drug or radiation to the disease site. Positron Emission Tomography (PET) can provide three dimensional positioning of the location of positron emitting radioisotopes that can mark a disease site. However, the inversion of the raw emission projection data into a 3D volume is computationally intensive, and this results in a low update or frame rate. In order to be useful in either guiding a surgeon, or some other automated feedback approach, the update/frame rate must be of sufficient speed that the user can effectively control the process. This approach provides a substantial improvement to the frame rate by taking advantage of iterative reconstruction methodologies to shortcut the reconstruction process.

19 Claims, 2 Drawing Sheets

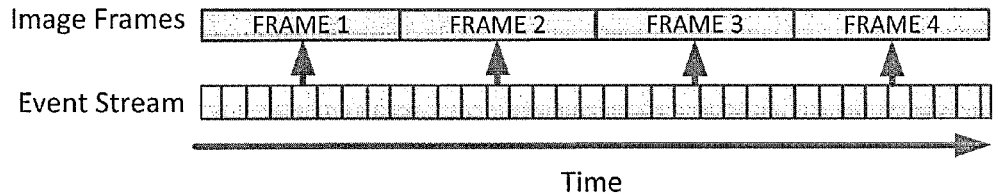
FIG. 1—Idealized frame rate based on a fully supporting event stream.
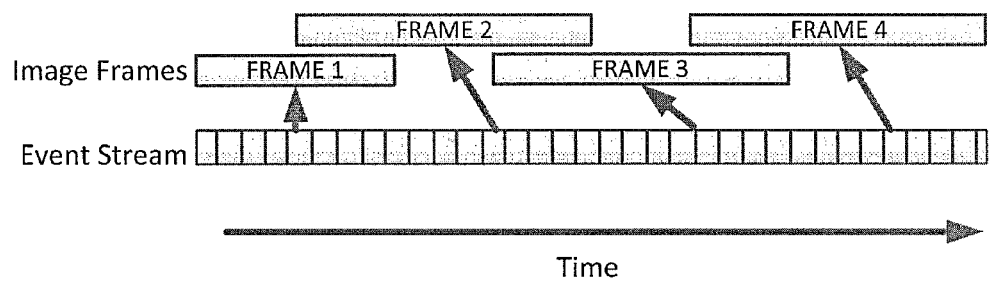
FIG. 2—Frame duration limited by statistics in the event stream causes longer frame times. This results in overlap, and thus temporal blurring (phosphorescence).
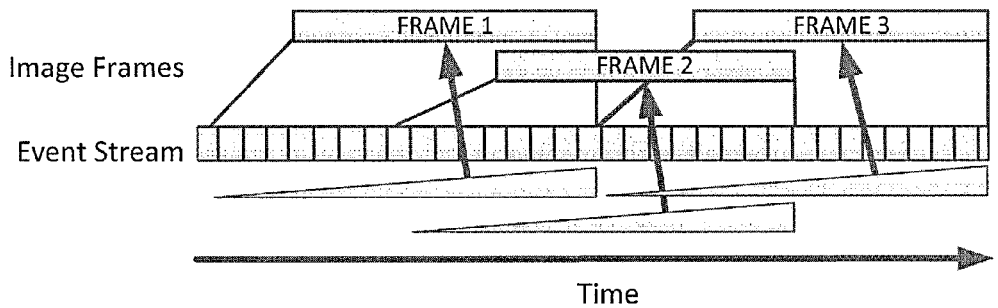
FIG. 3—Event formation is weighted with respect to time before being incorporated into the current image frame.

EMISSION COMPUTED TOMOGRAPHY FOR GUIDANCE OF SAMPLING AND THERAPEUTIC DELIVERY

CROSS-REFERENCE TO RELATED APPLICATION

This application claims priority to and the benefit of U.S. Provisional Patent Application No. 61/556,590, filed on Nov. 7, 2011. The entirety of the provisional patent application is hereby incorporated by reference to the fullest extent allowable.

BACKGROUND

Image guided drug and therapy delivery is used to optimize therapeutic delivery to a given diseased area. Standard fluoroscopy, MR, CT, and ultrasound have been used for a number of years to perform guided biopsies and delivery of drugs to a variety of locations in the body. See, for example, Mullar D A, Carrasco C H, Katz R L, et al., "FNAB: the role of immediate cytologic assessment," American Journal of Roentgenology 1986; 147:155-58; Moullen I S, Merc P R., "Percutaneous coaxial biopsy technique with automated biopsy needle—value in improving accuracy and negative predictive value" Radiology 1993; 186:515-22; Zinzani P L, Colecchia A, Fest D, et al., "US guided core needle biopsy is effective in initial diagnosis of lymphoma" Hematologica 1998; 83:989-92; Mouton J S, Leoni C J, Quarfardt S D, Woth S., "Percutaneous image guided biopsy" In Baum S, Pentcort M (ed). Abrams Angiography: Interventional Radiology, 2nd edition, Lippincot William Wilkins, 2006. Philadelphia, pp 255-78; Prashant, Ramachandra C Pattbhiraman, et al., "Feasibility, Safety, and efficacy of the CT guided Fine needle aspiration cytology (FNAC) of lung lesions" Ind J Med & Paed Oncol 2007; 28:16.

These modalities are anatomical in nature, namely, they represent the physical state of the tissue, not its functional state. Emission computed tomography imaging modalities such as Positron Emission Tomography (PET) represent the function of the tissue, and can present more information to the clinician. For example, within a cancerous tumor, anatomically, the center is no different than the outer edges, but depending on the type of cancer, it may in fact be necrotic. Samples taken from this area may produce erroneous results. This means that simply targeting the larger central portion of the tumor is not adequate in all cases. FluoroDeoxyGlucose (FDG) studies done with PET can differentiate between necrotic and active areas of a cancerous tumor.

Traditional image-guided navigation systems have relied on tracking of the instrument and images taken prior to the procedure to guide the instrument to a particular place. MR, CT, fluoroscopic, PET and other types of images have been used. However, soft-tissue in many parts of the body rarely remains in the same location when the patient is moved. Indeed, the instrument itself can sometimes displace the tissue enough to miss the target. If guidance down to a millimeter is desired, traditional image-based navigation systems therefore may not be suitable for at least some types of procedures.

It has been hypothesized that by injecting the patient with FDG, and using a needle that is coated with a positron emitting radioisotope, PET can be used to guide the needle directly to the diseased area. Once properly located, a biopsy sample can be taken, or a therapeutic can be delivered. The PET breast imaging company, Naviscan, has done work along these lines. See Xiaohong, Anashkin, Matthews, Weidong, Real-Time Viewer for Positron Emission Mammography Guided Biopsy, IEEE Transactions on Nuclear Science, 57:3, June 2010, pp. 1139-1145. Its approach uses fixation, and it is very approximate.

It is not necessary to guide a physical device to deliver a therapeutic. In fact, radiation therapy can perform similar therapeutic delivery, and the use of PET scans to plan radiation therapy is standard practice. See Gregoire V, Haustermans K, Geets X, et al., "PET-based treatment planning in radiotherapy: a new standard?" J Nuc. Med. 2007; 48:68S-77S. Some radiation treatment techniques, namely proton therapy, are powerful enough that they activate Carbon, Nitrogen, and Oxygen atoms as they pass through the body. As these activated isotopes decay, some of them give off positrons which can be imaged with PET. Thus, it is theoretically possible to see the effect of proton therapy with PET, and relate the location of the activated isotopes with the delivery of therapeutic radiation.

Due to difficulties steering the proton beam, as mentioned by Peterson, Polf, Ciangaru, Frank, Bues, Smith, "Variations in proton scanned beam dose delivery due to uncertainties in magnetic beam steering" Med. Phys., 36(8), 2009, pp. 3693-3702, it is desirable to perform an incremental approach to this type of therapy. The presence of bone, fat, muscle, and metal implants can substantially alter the beam path, causing the beam to miss the target. In this method, a theoretically computed beam profile of very low dose would be initially performed. Once the resulting PET scan identified the actual target, the beam parameters could be altered to steer the beam through the body to the ideal location without regard to distortion. Feedback during the process would keep the beam on the precise target.

BRIEF DESCRIPTION OF THE DRAWINGS

FIG. 1 is a representation of an idealized frame rate based on a freely supporting event stream.

FIG. 2 is a representation of a stream of coincident event data from detectors of a PET scanner, in which a frame duration is limited by statistics of the event stream, resulting in longer time frames. This results in overlap of the frames, and thus temporal blurring.

FIG. 3 is a representation illustrating framing of data from detectors of a PET scanner, in which event information is weighted with respect to time being incorporated into a current image frame.

DETAILED DESCRIPTION

Figure 4:
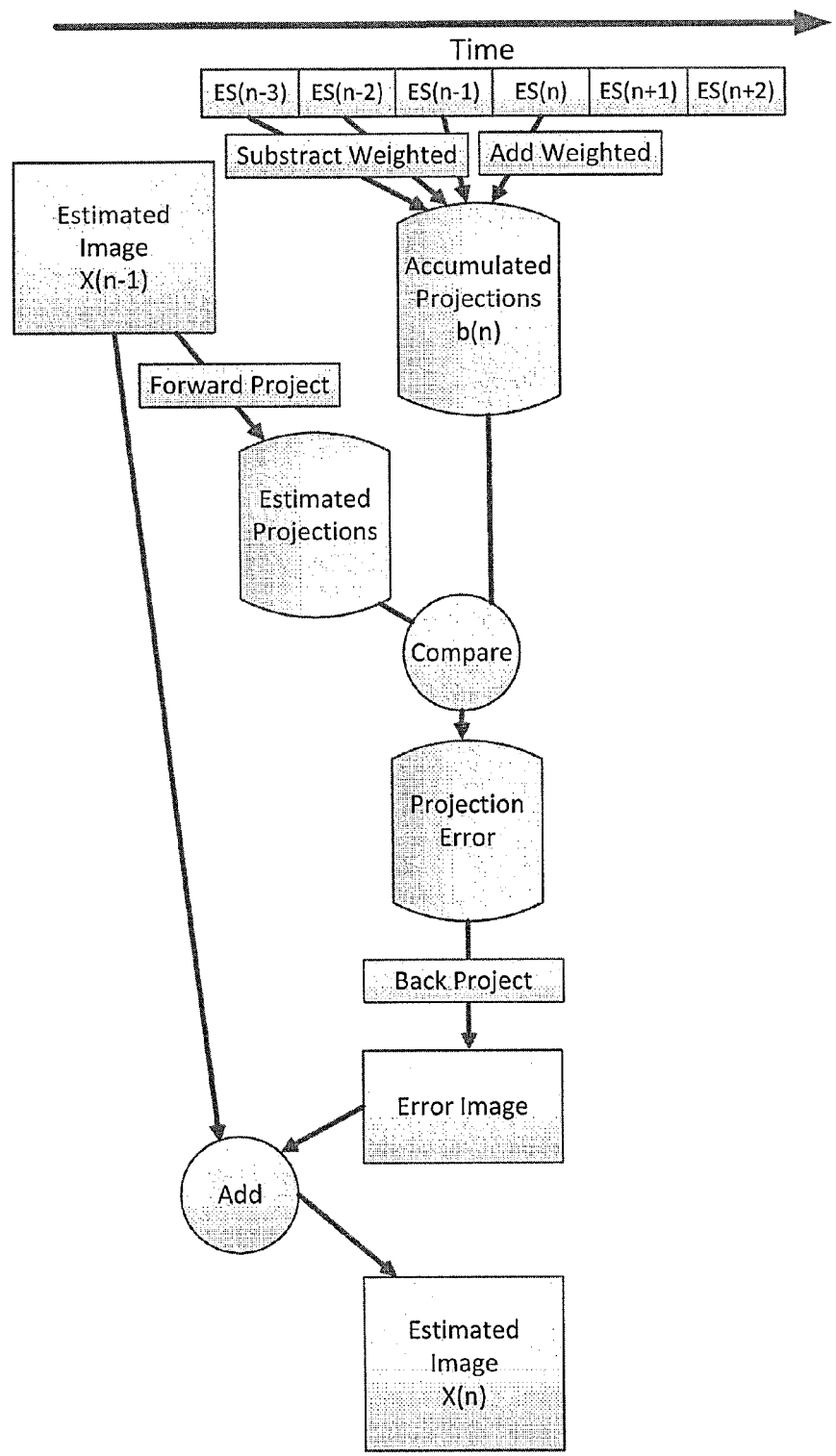
FIG. 4 is a flow diagram illustrating a process for combining incoming coincident event data from a PET scanner with a prior estimated image to create a new estimated image.

The accuracy, and thus effectiveness of any image guided technique is a function of the update rate. The faster that targeting information, and provide updated feedback, the easier it is for the clinician to steer the needle or the medical physicist to steer the proton beam. With improved feedback it becomes possible to perform these types of operations in a fully automated fashion. For this reason, it is important to go as fast as possible, preferably with image frame durations less than one second.

In an ideal case, a stream of events would be interpreted to generate a series of image frames that would meet the requirements. This is shown in FIG. 1.

PET is a 3D modality, acquiring all image planes simultaneously in a statistical, counting type approach, where each event is separately counted. A PET scanner is typically comprised of a ring of detectors for detecting the events and various processors for processing signals from the detectors and reconstructing three-dimensional images that are then formatted for display on a display associated with the scanner or other display. The entire image volume is reconstructed in a single step as the individual events are accumulated. Due to this limitation, the rate at which the measured volume can be updated is limited to the speed of the 3D reconstruction method used.

There are thus at least two problems that must be resolved. The first is a statistical limitation. The statistical limitation is formed because a certain number of event counts must be acquired to achieve a given level of image quality. Just as the estimation of a population in statistics requires a given number of samples to measure a characteristic, PET is the same. Unfortunately, an unlimited number of counts cannot be acquired in a finite, and in this case relatively small, period of time. Depending on the count rate, a variable amount of memory must be employed to maintain the necessary statistical integrity so that the image is reliable. This lag can be seen as time delayed blurring. It will result in ghosting across the display if something moves quickly through the field of view.

FIG. 2 shows the relative relation in time for the image frame we can visibly see, and the information content present necessary to reconstruct an image volume. Ideally, the time window for the desired frame would match and no blurring would occur, as in FIG. 1, but we can only guarantee this to be the case under exceptionally high count rate conditions and this would result in more radiation dose than necessary to the patient.

Under an FDG targeting PET scan, the tumor itself is not moving. Therefore, except for the needle, blurring is not a problem. The needle is relatively small, and the amount of activity per unit volume of the needle can be quite high. Therefore, the ability of the system to determine the location of the needle can, in theory, be good. Weighting the contribution of the events within the time window to change the contribution of older events resolves this issue. This approach is shown in FIG. 3. The target location is unaffected (it isn't moving), and the needle itself has high enough statistics that the location is well resolved. From a clinical usage standpoint, simply stopping momentarily will clear any ghosting on the display.

The second problem to be overcome is the speed at which the computational work can be done to compute the next image in the frame sequence.

Analytical approaches to performing reconstruction, such as Filtered Back Projection (FBP), can take the raw information for an image volume and directly compute a result. They are often used in anatomical modalities such as Computed Tomography (CT). See, for example, Kak, Slaney, "Principles of Computerized Tomographic Imaging," SIAM, #2008. These approaches do not perform well with limited statistics, and the resulting streak artifacts make interpretation difficult. Even as fast as they are, they are still not fast enough to achieve subsecond frame rates in a modern, high resolution PET scanner. Iterative approaches to reconstruction use linear algebra based mathematical techniques to estimate the answer, then refine that answer successively to come to a result. See, for example, Kak, Slaney, "Principles of Computerized Tomographic Imaging," SIAM, 2008. The result is never exactly right, and is thus referred to as the volume estimate, but it can be close, depending on the convergence criteria that has been established.

The time required to converge upon the correct answer is dependent principally on two items. First, how close to correct is the current volume estimate. A volume estimate that is very similar to the actual "true" volume will involve very little change to the next iteration, thus they will converge rapidly, within error limits. Secondly, the amount of work needed to compute the next iteration can be more limited than, say, the one cycle needed by an analytic approach. Conceptually, FBP can be considered to be iterative in the sense that they start with a blank volume estimate, then go through one very complex iteration to achieve a converged result. True iterative approaches can be thought of as a simpler, less thoughtful variation on that technique, which are less complex, and thus faster per iteration, but they require more iterations to perform the same end result, normally requiring a longer total time to achieve a similar result.

The solution to the computation problem, the image volume for a given frame, can be expressed in terms of three variables in a linear system of equations.

$$Ax=b \quad (1)$$

In this case, x represents the estimated image volume, b is the coincidence event stream data, and A is a transform that relates the two. We sometimes refer to A as the system matrix. In this particular case, the system matrix A is not well behaved, and is not directly invertible, thus one of any number of iterative techniques can be used to solve it. These include, but are not limited to Jacobi, Newtonian, etc. In general, all of these approaches are a variation on the following, generalized technique.

Using the current image estimate, the estimated event stream data (also called projections) that would match the current image is computed. This is usually called forward projection. The error between the estimated event stream data and the actual event stream data is then computed. This error can be either a difference, or a ratio in the case of statistical methods. The computed error is projected into an image volume to create an error image. This process is usually called back projection. The error image estimate is then added to the current image estimate to determine a new current image estimate. This process is then repeated until the computed error is reduced to desirable or predetermined limits.

There are two of features of all of these approaches that can be exploited. First, the computational work required to perform a single iteration is relatively light, so subsequent updates occur rapidly. Second, if the prior estimated image differs in only minor ways to the new estimated image, the error will remain low and the estimated image will be a good approximation of the actual true value.

Integrating an iterative reconstruction approach with the continuous event stream to create a continuous set of image frames can provide faster frame rates with better image quality than can be done under other circumstances. A bulk of the image volume typically does not change from one frame to the next. Small changes mean that the image computed for a particular frame is a good candidate for the estimated image in the subsequent frame. In addition, the compute requirements for a small number of iterations—just a single iteration can be made in at least some circumstances—can be done in a short period of time.

The event stream data can be viewed as a continuous stream that is grouped into segments associated with the time that the image frame is acquired. Thus, for an image frame n, all of the events associated with that particular time frame only, is referred to as $ES_n$. Prior frames would thus be $ES_{n-1}$, $ES_{n-2}$, etc. The current estimated image for frame n is referred to as $x_n$ as per equation (1). Similarly, prior frames are referred to as $x_{n-1}$, $x_{n-2}$, etc. Accumulated coincident event data, also called projection information, is referred to as b, also as per equation (1).

Thus, in order to compute the estimated image for the current frame, the accumulated projection information is updated by adding the current frame event stream data and subtracting prior frames in a weighted fashion.

$$b_n = b_{n-1} + W_0 ES_n - W_1 ES_{n-1} - W_2 E_{n-2} - \quad (2)$$

The weights $W_n$ are chosen dependent on the application. The total magnitude of $b_n$ must be large enough to maintain the desired image quality. From equation (2), the magnitude of $b_n$ is dependent on the magnitudes of the various event data segments and their weights. The weights can represent any arbitrary mathematical function. Preferably, they are positive and sum to 2.0 in order to maintain consistency. For example, $W_0$ is set to 1.0, and the others to values less than 1.0 in a declining pattern.

Once the accumulated projections are computed for the current frame, the prior estimated image ($x_{n-1}$) is forward projected to compute the estimated projections. The accumulated projections are then compared against the estimated projections, and projection error determined. After back projecting the projection error, the resulting error image is added to the prior estimated image ($x_{n-1}$) to determine the current estimated image ($x_n$). If the magnitude of the projection error is too large, then the current estimated image can be fed back into the process for an additional iteration before finalizing $x_n$.

The overall process is exhibited as a flow chart in FIG. 4. Examples of applications include image guided biopsy, image guided drug delivery, and image guided steering of processes. The process would, for example, be implemented using one or more processors executing software of firmware program instructions stored on computer readable media. The processors could be general-purpose or special-purpose processors or application-specific processors or integrated circuits, or combinations of them. In applications using the foregoing reconstruction processes, the display is preferably near the gantry on which the subject rests. However, the display could also be worn by the clinician performing the procedure.

In an image guided biopsy, the subject is injected with an imaging agent (i.e. FDG, but others are possible as well) visible to PET, the diseased area becomes visible. Use of a biopsy needle or device that is manufactured of, coated, plated, or otherwise made to emit positrons allows both the lesion and the needle to be visible to the scanner in three dimensions. This can be displayed to the clinician either through a 2D video screen, or via 3D viewing techniques to give additional depth perception.

Similar to image guided biopsy, image guided drug delivery involves injecting the subject with an imaging agent (i.e. FDG, but others are possible as well) visible to PET, causing the diseased area to become visible. Use of a needle, drill, or other device that is manufactured of, coated, plated, or otherwise made to emit positrons allows both the lesion and the device to be visible to the scanner in three dimensions, allowing optimal positioning of the delivery mechanism. This can be displayed to the clinician either through a 2D video screen, or via 3D viewing techniques to give additional depth perception. Adding a positron emitting compound to the injection allows the evaluation of the extent of the injection during the injection process to ensure proper coverage.

Electronically controlled processes such as guided beam therapies that either generate positrons, or can be made to generate positrons as part of their operation can utilize the target information generated by the PET scanner to apply distortion corrections to the beam to accommodate variations in anatomy and the manufacturing physics of the device. Prior to scan, the patient could be optionally injected with a tracer to make the diseased area visible, then this signal could be subtracted before steering occurs. The speed advantage presented by this method could substantially enhance the feedback loop of attempting to control such a device in this manner.

The foregoing description is of examples embodying, at least in part, certain teachings of the invention. Alterations and modifications to the disclosed embodiments may be made without departing from the invention. The meaning of the terms used in this specification are, unless expressly stated otherwise, intended to have ordinary and customary meaning and are not intended to be limited to the details of the illustrated structures or the disclosed embodiments.

What is claimed is:

1. A method for reconstructing a series of image frames for display at a predetermined frame rate, from a stream of projection data from a detector of a tomographic emission scanner, the method comprising:
   receiving a continuous stream of projection information generated from tomographic emission detectors;
   dividing the projection information into a sequence of time-dependent segments, and, for a current frame, associating with it projection information from at least one segment;
   reconstructing an image for the current frame, the reconstructing of the image comprising:
      accumulating projection information from the at least one segment associated with the current image frame;
      comparing the accumulated projection information to estimated projection information that has been forward projected from an estimated image from a prior frame, and generating projection information error, the estimated image for the prior frame having been reconstructed based at least in part on one or more prior segments of projection information that does not include the projection data from the at least one segment associated with the current image;
      back projecting the projection information error to create an error image; and
      combining the error image and the estimated image from the prior frame to generate an estimated image for the current frame; and
   displaying the estimated image for the current time frame.

2. The method of claim 1, wherein accumulating projection information includes accumulating projection information from the at least one segment associated with the current frame and from a predetermined number of prior segments of projection information.

3. The method of claim 2, wherein accumulating projection information further comprises weighing the projection information for each segment being accumulated according to predetermined weights.

4. The method of claim 3, wherein the predetermined weights are time-dependent, with the most weight being given to the at least one segment associated with the current frame and successively less weight for each prior segment.

5. The method of claim 3, wherein the accumulating of projection information comprises:
   adding the projection information from the at least one segment associated with the current frame to the projection information accumulated for the prior frame; and
   subtracting projection information from the predetermined number of prior segments in a weighted fashion.

6. The method of claim 1, further comprising, iterating the reconstructing of the image for the current frame using the last estimated image for the current frame in place of the estimated image from the prior frame until the projection information error is within predetermined limits.

7. A non-transitory computer readable media carrying instructions that, when read by a computer, cause the computer to perform a process according to claim 1.

8. A computed tomographic scanner, comprising:
  detectors for generating a stream of projection information;
  one or more processors specially adapted for sequentially reconstructing from the projection information a series of time-dependent, three dimensional image frames for display at a predetermined frame rate, reconstructing comprising:
    dividing the projection information into a sequence of time-dependent segments, and, for each frame, associating with it at least one segment of projection information;
    reconstructing an image for the current frame, the reconstructing of the image for the current image frame comprising:
      accumulating projection information from the at least one segment associated with the current image frame;
      comparing the accumulated projection information to estimated projection information that has been forward projected from an estimated image from a prior image frame, and generating projection information error, the estimated image from the prior image frame having been reconstructed based at least in part on one or more prior segments of projection information that do not include the projection data from the at least one segment associated with the current image;
      back projecting the projection information error to create an error image; and
      combining the error image and prior estimated image to generate an estimated image for the current frame; and
  a display for displaying reconstructed images at the predetermined frame rate.

9. The computed tomographic scanner of claim 8, the accumulating includes accumulating projection information from the at least one segment associated with the current image frame and from a predetermined number of prior segments of projection information.

10. The computed tomographic scanner of claim 9, wherein accumulating projection information further comprises weighing the projection information for each segment being accumulated according to predetermined weights.

11. The computed tomographic scanner of claim 10, wherein the predetermined weights are time-dependent, with the most weight being given to the at least one segment associated with the current frame and successively less weight for each prior segment.

12. The computed tomographic scanner of claim 10, wherein the accumulating of projection information comprises:
  adding the projection information from the at least one segment associated with the current frame to the projection information accumulated for the prior frame; and
  subtracting projection information from the predetermined number of prior segments in a weighted fashion.

13. The computed tomographic scanner of claim 8, wherein the one or more processors adapted for, if the generated projection information error is not within predetermined limits, iterating the reconstructing of the image for the current frame for the current frame using the last estimated image for the current frame in place of the estimated image from the prior frame.

14. An apparatus, comprising:
  detectors for generating a stream of projection information;
  means for sequentially reconstructing from the projection information a series of time-dependent, three dimensional images for display at a predetermined frame rate, comprising:
    means for dividing the projection information into a sequence of time-dependent segments, and, for each frame, associating with it at least one segment of projection information;
    means for each current frame, reconstructing a current image, the reconstructing of the current image comprising:
      means for accumulating projection information from the at least one segment associated with the current image frame;
      means for comparing the accumulated projection information to the estimated projection information that has been forward projected from an estimated image from a prior frame, and generating projection information error, the estimated image for the prior frame having been reconstructed based at least in part on one or more prior segments of projection information that does not include the projection data from the at least one segment associated with the current image;
      means for back projecting the projection information error to create an error image; and
      means for combining the error image and prior estimated image to generate an estimated image for the current frame; and
  a display for displaying reconstructed images at the predetermined frame rate.

15. The apparatus of claim 14, wherein the means for accumulating accumulates projection information from the at least one segment associated with the current frame and from a predetermined number of prior segments of projection information.

16. The apparatus of claim 15, wherein means for accumulating projection information further comprises weighing the projection information for each segment being accumulated according to predetermined weights.

17. The apparatus of claim 16, wherein the predetermined weights are time-dependent, with the most weight being given to the at least one segment associated with the current frame and successively less weight for each prior segment.

18. The apparatus of claim 15, wherein the means for accumulating of projection information comprises:
  means for adding the projection information from the at least one segment associated with the current frame to the projection information accumulated for the prior frame; and
  means for subtracting projection information from the predetermined number of prior segments in a weighted fashion.

19. The apparatus of claim 14, further comprising, means for iterating the reconstructing of the image for the current frame using the last estimated image for the current frame in place of the estimated image from the prior frame until the projection information error is within predetermined limits.

\* \* \* \* \*